United States Patent [19]

Jongsma

[11] 4,227,017

[45] Oct. 7, 1980

[54] PROCESS FOR THE PREPARATION OF AN ALKALI-METAL BENZOATE BESIDES A BENZYL ALCOHOL

[75] Inventor: Cornelis Jongsma, Oirsbeek, Netherlands

[73] Assignee: Stamicarbon, B.V., Geleen, Netherlands

[21] Appl. No.: 40,152

[22] Filed: May 17, 1979

[30] Foreign Application Priority Data

May 19, 1978 [NL] Netherlands .......................... 7805415

[51] Int. Cl.$^2$ ....................... C07C 51/42; C07C 29/00
[52] U.S. Cl. ...................................... 562/494; 568/810
[58] Field of Search ......................... 562/494; 568/810

[56] References Cited

U.S. PATENT DOCUMENTS

| 2,568,095 | 9/1951 | Smith et al. ........................... 562/494 |
| 3,078,303 | 2/1963 | Sweeney ............................... 562/494 |

Primary Examiner—Alan Siegel
Attorney, Agent, or Firm—Cushman, Darby & Cushman

[57] ABSTRACT

An alkali-metal benzoate is prepared besides benzyl alcohol from a contaminated benzyl benzoate reaction residue obtained in the oxidation of a monoalkyl-benzene compound with a gas containing molecular oxygen. The disclosed process provides for distillation of the contaminated benzyl benzoate in the presence of a basic substance and the resulting distillate is hydrolyzed using an alkali-metal base.

In this way, the benzyl benzoate that previously could not be separated from certain tar components by distillation is converted into a pure alkali metal benzoate such as sodium benzoate, besides pure benzyl alcohol, so that a waste product that was previously useless is converted into useful substances.

14 Claims, No Drawings

PROCESS FOR THE PREPARATION OF AN ALKALI-METAL BENZOATE BESIDES A BENZYL ALCOHOL

BACKGROUND OF THE INVENTION

The invention relates to a process for the preparation of an alkali-metal benzoate, more in particular sodium benzoate, besides benzyl alcohol by hydrolysis of a benzyl benzoate.

A special object of the invention is to provide a suitable method of processing a contaminated benzyl benzoate obtained in the oxidation of a monoalkyl-benzene compound with a gas containing molecular oxygen. The oxidation of toluene is effected on a technical scale, and the benzyl benzoate then formed is the unsubstituted benzyl benzoate, i.e., both benzene rings of the benzyl benzoate are unsubstituted. Because of this technical importance, the present invention will be explained primarily with reference to the toluene oxidation and the contaminated unsubstituted benzyl benzoate so obtained. However, it will be understood that the present invention can also be applied to contaminated substituted benzyl benzoates that, for instance, may form, in the oxidation of other alkyl benzene compounds, particularly those having 1 to 4 carbon atoms in the alkyl group, whose benzene ring may contain other non-interfering substituents, for instance, one or more halogen, nitro or sulphonic-acid substituents. Examples include ethyl benzene, p-chlorotoluene, p-nitrotoluene, and p-toluene sulphonic acid.

The oxidation of toluene, referred to above, may be conducted either in the liquid phase with, e.g., a cobalt and/or manganese salt that is soluble in the reaction medium as a catalyst, or in the gaseous phase with, e.g., a catalyst based on an oxide of vanadium or another transition metal according to art-recognized procedures as described in Stanford Research Institute (SRI) reports No. 7 (1965), 29; 7A (1968), 241; No. 7B (1976), 53.

Part of all of the benzoic acid, together with all of the lower boiling point products, can be distilled from the reaction mixture. This reaction mixture contains benzoic acid, benzyl benzoate and other products with a higher boiling point than benzoic acid which products are jointly referred to herein as tar residue as well as unconverted toluene and by-products with a boiling point lower than benzoic acid, such as benzyl alcohol and benzaldehyde. The materials distilled from the reaction mixture can be processed further to isolate pure benzoic acid, so that contaminated benzyl benzoate remains as a residue in the form of a tar that may also contain benzoic acid. This residue may be used as the starting material for the process according to the present invention and from the viewpoint of commercial practice is the preferred starting material.

Contaminated benzyl benzoate that may also be used as a starting material for the process according to the present invention can also be formed when the distillate described above is heated, optionally in the presence of an esterification/re-esterification catalyst, such as sulfuric acid, phosphoric acid, boron trifluoride or zinc acetate, in order to esterify or re-esterify any benzyl alcohol and/or light benzyl esters, such as benzyl formiate and benzyl acetate, into benzyl benzoate. Annoying contaminations are formed especially when the mixture still contains benzaldehyde during this ester forming reaction.

It is very difficult to recover useful products from such a contaminated benzyl benzoate. Benzyl benzoate may be separated from the tar residue by distillation, but a pure benzyl-benzoate product can hardly be obtained in this manner. The present applicant has found that the component fluorenone of the tar gives rise to special difficulties, for it appears that it is virtually impossible to separate fluorenone from benzyl benzoate. In addition to fluorenone, other unidentified compounds may play a part as well. For instance, while it is possible to hydrolyze the benzyl benzoate, if so desired after it has been distilled from the tar residue, into benzyl alcohol and sodium benzoate using, for instance, aqueous sodium hydroxide solution, the sodium benzoate is very difficult to recover in a pure form, as some impurities persistently combine with it. Sodium benzoate in a pure form is an important and valuable commercial product for which there is a substantial market. One of its uses is as an important preservative.

DETAILED DESCRIPTION OF THE INVENTION

According to the present invention, an alkali-metal benzoate besides benzyl alcohol, is prepared from a contaminated benzyl benzoate reaction residue obtained in the oxidation of a monoalkyl-benzene compound with a gas containing molecular oxygen by distilling the contaminated benzyl benzoate in the presence of a basic substance, in an amount sufficient to accomplish an adequate purification of said benzyl benzoate, and thereafter hydrolyzing the distillate obtained with an alkali-metal base.

In this way, a pure alkali metal benzoate can be obtained from the contaminated benzyl benzoate. Using a relatively direct procedure, benzyl alcohol can also be recovered in a pure form from the hydrolyzed mixture. Benzyl alcohol is a useful product which is utilized in flavoring and perfumery. The process according to the present invention consequently uses a virtually useless waste product and converts it into two useful substances.

The basic substance used in the distillation of the benzyl benzoate may be, for example, an oxide, hydroxide or carbonate of an alkali or alkaline-earth metal, ammonia, an amine, an ammonium salt with or without a substituent at the nitrogen atom, or an amide. Preferably, there is used (solid) sodium hydroxide, sodium carbonate, potassium hydroxide, potassium carbonate, calcium hydroxide, calcium oxide, ammonia, and, in particular, an ammonium carbonate. When an amine used, it is preferably aliphatic and, preferably, a primary amine having preferably from 1 to 6 carbon atoms per alkyl group. Examples include methyl amine, ethyl amine, propyl amine, isopropyl amine, butyl amine, isobutyl amine, cyclopentyl amine or cyclohexyl amine. Also salts of ammonia and of these amines e.g. substituted or unsubstituted ammonium compounds, that can decompose under the distillation conditions, e.g., the hydrogen carbonates, carbonates, formiates, acetates, and benzoates, can be used advantageously. The amide may be, e.g., a carboxylic acid amide, preferably urea. In order to accomplish an adequate purification of the impure benzyl benzoate, the basic substance used as herein defined is mostly used in an amount of about 0.01 to about 10% by weight of the impure benzylbenzoate, preferably, in an amount of about 0.5 to about 5% by weight of the impure benzyl benzoate.

The distillation may be effected at approximately atmospheric or even at a slightly elevated pressure, for instance, up to 200 kPa, but preferably at reduced pressures, of the order of about 0.1 to about 10 kPa. The distillation temperature is usually in the range of about 80° to about 240° C. dependent upon the pressure conditions employed.

Hydrolysis of the distillate is preferably accomplished with a basic solution, particularly aqueous sodium hydroxide or, if so desired, a soda solution. One can also use another alkali-metal base, for instance, potassium hydroxide or potassium carbonate. However, there exists a definite market for sodium benzoate, so for economic reasons sodium benzoate is the desired reaction product. Accordingly, the hydrolysis is preferably effected with a basic sodium compound. The temperature during the hydrolysis reaction may be between about 30° and about 200° C. The pressure is not critical and for practical reasons, preferably is between 100 and 1000 kPa although higher and lower pressures may be used.

After the hydrolysis, the resulting benzyl alcohol may be separated, e.g., by distillation, e.g., steam distillation. The alkali-metal benzoate can be recovered in the solid form by crystallization from the aqueous solution.

In most cases, the hydrolysis mixture contains some annoying organic impurities together with the desired benzyl alcohol and alkali-metal benzoate. If such is the case, the hydrolysis mixture is preferably extracted with an organic extraction agent that causes liquid phase separation with the hydrolysis reaction mixture. In this separation, the benzyl alcohol and the organic impurities pass into the organic phase, while the aqueous phase is a virtually pure solution of alkali-metal benzoate, from which pure solid alkali-metal benzoate can be recovered in a simple way. Pure benzyl alcohol and the extraction agent can be recovered from the organic phase by distillation.

Examples of suitable organic extraction agents are aliphatic, aromatic, and mixed aliphatic-aromatic hydrocarbons with, preferably, at most 12 carbon atoms per molecule, ethers, esters, and halogenated especially, chlorinated or brominated hydrocarbons with normal boiling points, preferably not exceeding 250° C. Specific examples include gasoline, heptane, benzene, toluene, the xylenes, diisopropyl ether, amyl acetate, ethyl benzoate, chloroform, 1,2-dichloroethylene, 1,1,1-trichloroethane, and 1,2-dibromomethane. Special preference is given to toluene, as it is available in large quantities in a toluene oxidation plant and ensures proper separation and recovery of very pure benzyl alcohol.

According to a suitable embodiment of the process according to the present invention, the product mixture of the hydrolysis reaction is fed into an extraction column, which is also supplied with the extraction agent and the extraction step is conducted.

Another embodiment is for the extraction agent to be already present during the hydrolysis reaction. It will be apparent that in this case it is preferable to select an extraction agent that is inert under the reaction conditions in question. After the reaction, the product mixture is separated into an organic layer containing the benzyl alcohol, various organic impurities and the extraction agent itself and an aqueous layer containing the alkali-metal benzoate.

The hydrolysis reaction can then be effected in an extraction column through which the benzyl benzoate distilled in the presence of a basic substance and the basic solution are passed in countercurrent relation to the extraction agent. Other arrangements for the extraction will be apparent to those skilled in the art.

The present invention will now be described with reference to the following Examples which illustrate but do not restrict the invention herein described.

EXAMPLE 1

The liquid reaction product of the oxidation of toluene with air in the liquid phase in the presence of cobalt acetate as a catalyst (degree of toluene conversion being about 20% by weight) was distilled until virtually all benzoic acid and lower-boiling components were removed from the reaction product. The residue was subjected to film evaporation at a temperature of 230° C. and a pressure of 7 kPa. The distillate obtained in the film evaporation, which was a mixture of benzyl benzoate, some benzoic acid and tar (as described above), was distilled again, this time in the presence of 3% by weight of solid ammonium hydrogen carbonate, calculated to the amount of distillate obtained in the film evaporation, and at a temperature of 140° C. and a pressure of 0.8 kPa.

Sodium hydroxide (20% by weight), calculated on the quantity of distillate, was added to the distillate in the form of an aqueous solution of sodium hydroxide (14% by weight of NaOH) and the entire mixture was stirred for 30 minutes at 100° C. under reflux conditions. Virtually all benzyl benzoate will then have been hydrolyzed.

After cooling, the reaction mixture was extracted four times with equal portions of toluene, the total amount applied being equal to twice the weight of the water present. The toluene layers thus obtained were combined and washed with water (10% by weight relative to the amount of toluene present). After separation of the layers the washing water is added to the above-mentioned aqueous layer.

Benzoic acid was added to the combined aqueous layer in order to neutralize any free sodium hydroxide still present. Next, the reaction mixture was distilled with steam, after which solid sodium benzoate was separated off virtually quantitatively by removal of water.

A solution of the sodium benzoate thus obtained passed the color test of the Dutch pharmacopoeia. The sodium benzoate also met the requirements of the sulfuric-acid test DAB 7 of the German pharmacopoeia.

The toluene and the water present were distilled from the washed toluene layer at atmospheric pressure. Next, the residue was distilled at 70° C. and 1 kPa. The top flow from this distillation consisted of virtually pure benzyl alcohol (purity over 99% by weight). The yield of benzyl alcohol after distillation relative to the benzyl benzoate amounts to over 90%.

EXAMPLE 2

Experiment 1 was repeated, however, this time the ammonium hydrogen carbonate was replaced by solid sodium hydroxide in an amount of 3% by weight calculated to the distillate obtained in the film evaporation.

As with the previous Example, the resulting sodium benzoate passed the purification tests and was obtained virtually quantitatively. Additionally, virtually pure benzyl alcohol was obtained in a yield of over 90% relative to the benzyl benzoate.

What is claimed is:

1. A process for recovering sodium benzoate besides benzyl alcohol from a reaction residue resulting from the manufacture of benzoic acid by the oxidation of toluene and containing contaminated benzyl benzoate therein, said process consisting essentially in:
   (a) distilling said residue containing contaminated benzyl benzoate therein at a temperature in the range of about 80° C. to about 240° C. and in the presence of from about 0.01 to about 10% by weight of a basic substance calculated on the weight of said residue being distilled;
   (b) hydrolyzing the distillate resulting from step (a) with an aqueous solution of sodium hydroxide or sodium carbonate at a temperature in the range of about 30° C. to about 300° C. thereby producing an aqueous solution containing the sodium benzoate and benzyl alcohol;
   (c) crystallizing and recovering the sodium benzoate from the resulting solution of step (b); and
   (d) distilling and recovering the benzyl alcohol from the resulting solution of step (b).

2. A process for the preparation of an alkali-metal benzoate besides a benzyl alcohol, from a contaminated benzyl benzoate reaction residue obtained in the oxidation of a monoalkyl-benzene compound with a gas containing molecular oxygen, wherein the contaminated benzyl benzoate is distilled at a pressure of about 0.1 kPa to about 200 kPa and in the presence of a basic substance selected from the group consisting of oxides, hydroxides and carbonates of alkali or alkaline-earth metals, ammonia, an amine, an ammonium salt that is optionally substituted at the nitrogen atom, an amide and mixtures thereof, in an amount sufficient to accomplish an adequate purification of said benzyl benzoate which amount is at least 0.01% by weight of said basic substance calculated on the weight of said residue being distilled, and the obtained distillate is hydrolyzed at a temperature of about 30° C. to about 200° C. with an alkali-metal base.

3. The process according to claim 2 wherein the basic substance used in the distillation is an ammonium carbonate.

4. The process according to claim 2 wherein the basic substance used in the distillation is sodium hydroxide.

5. The process according to claim 2 wherein the basic substance used in the distillation is a primary aliphatic amine having from 1 to 6 carbon atoms.

6. The process according to claims 2 wherein the basic substance used in the distillation is urea.

7. The process according to claim 2 wherein the hydrolysis reaction is conducted with sodium hydroxide or sodium carbonate and the sodium benzoate is recovered from the product mixture.

8. The process according to claim 7 wherein the product mixture is extracted with an organic extraction agent and the benzyl alcohol is recovered from the extract.

9. The process according to claim 8 wherein the extraction agent is toluene.

10. The process according to claim 8 wherein the hydrolysis reaction is conducted in the presence of an extraction agent.

11. The process according to claim 2 wherein the amount of said basic substance is up to 10% by weight of said residue being distilled.

12. The process according to claim 11 whrein the amount of said basic substance is from about 0.5 to about 5% by weight.

13. The process according to claim 2 wherein said pressure is in the range of about 0.1 to about 10 kPa.

14. The process according to claim 2 wherein said distillation is conducted at a temperature in the range of about 80° C. to about 240° C.

* * * * *